United States Patent [19]

Barfurth et al.

[11] Patent Number: 4,924,016

[45] Date of Patent: May 8, 1990

[54] CONDENSED ACETOACETIC ACID ESTER TITANIUM CHELATES AND PROCESS FOR THEIR PREPARATION

[75] Inventors: Dieter Barfurth, Troisdorf-Spich; Heinz Nestler, Troisdorf-Eschmar, both of Fed. Rep. of Germany

[73] Assignee: Huels Troisdorf AG, Troisdorf, Fed. Rep. of Germany

[21] Appl. No.: 268,897

[22] Filed: Nov. 8, 1988

[30] Foreign Application Priority Data

Nov. 19, 1987 [DE] Fed. Rep. of Germany ....... 3739174

[51] Int. Cl.$^5$ .............................................. C07F 7/28
[52] U.S. Cl. .................................................... 556/40
[58] Field of Search .......................................... 556/40

[56] References Cited

U.S. PATENT DOCUMENTS

| 4,313,851 | 2/1982 | Barfurth et al. | 556/40 |
| 4,578,487 | 8/1986 | Barfurth et al. | 556/40 |
| 4,609,746 | 9/1986 | Barfurth et al. | 556/40 |
| 4,647,680 | 3/1987 | Barfurth et al. | 556/40 |

Primary Examiner—Paul F. Shaver
Attorney, Agent, or Firm—Felfe & Lynch

[57] ABSTRACT

Titanium chelates with 1 to 2 acetoacetic acid ester ligands and one to two alkoxy groups per titanium atom the sum of these ligands and the alkoxy groups being three as well as Ti-O-Ti bridge between two titanium atoms are formed by release of alcohol and condensation of mono- or bis-acetoacetic acid ester-Ti-(IV)-chelates which have up to 4 alkoxy groups per titanium atom.

3 Claims, No Drawings

CONDENSED ACETOACETIC ACID ESTER TITANIUM CHELATES AND PROCESS FOR THEIR PREPARATION

FIELD OF THE INVENTION

This invention relates to alcohol-free acetoacetic acid ester chelates of titanium-IV, and to a process for their preparation from the monomeric starting materials diisoproxybis(ethylacetoacetato)-titanium triisopropoxy-ethylacetoacetato-titanium by reaction with water and removal of the liberated alcohol by distillation.

BACKGROUND OF THE INVENTION IN THE PRIOR ART

Titanic acid alkyl esters have for a long time been known as cross-linking agents for high-molecular compounds comprising hydroxyl groups which can thereby be transformed into gels and plastic or elastic masses. Since lower alkyl esters of titanic acid generally react very rapidly with the indicated hydroxyl compounds, for example immediately upon admixing of the components or already prior to their use in the storage containers, titanium ester chelates whose reactivity has been decreased to the desired degree are often used in their place. Known chelate formers are, for example, acetoacetic acid ethyl ester, and a conventional titanium ester chelate formed with the latter compound is diisopropoxy-bis(ethylacetoacetato)-titanium (I), prepared by reaction of tetraisopropyl titanate of the formula $Ti(OC_3H_7)_4$ with two equivalents of acetoacetic acid ethyl ester of the formula $CH_3COCH_2COOC_2H_5$. This compound I is initially obtained as a liquid, but it often solidifies not only when it is cooled but also at room temperature, and then has a melting point of 25° to 28° C.

This behavior of compound I is often annoying when it is used, because as a rule it requires a device for liquefying of the product prior to admixture with the other normally liquid components of a reaction batch, and the required manipulation of heating and homogenizing connected therewith.

In order to overcome this disadvantage, U.S. Pat. 4,478,755 already proposes to completely or partially distill off the isopropyl alcohol liberated by the above described reaction between the titanate and the acetoacetic acid ester, and to replace the missing amount with other alcohols such as methyl or butyl alcohol, or to start from a mixture of different alkyl titanates and in this manner liberate different alcohols by the reaction. Both methods are said to make it possible to prepare cold-resistent solutions of the titanium chelate I in alcohols.

In certain practical applications of such titanium chelates, for instance as condensation or hardening catalysts in silicone compositions, such as those which are described in German Pat. 22 28 883, the presence of such lower alcohols would be detrimental.

OBJECTS OF THE PRESENT INVENTION

It is an object of the present invention to provide modifications of compound I which have a reduced tendency to crystallize but at the same time do not exhibit a noticeably altered reactivity.

Other objects and advantages of the instant invention will become apparent as the description thereof proceeds.

DESCRIPTION OF THE INVENTION

We have discovered that condensation products of compounds I meet these requirements. Such condensation products are formed by partially hydrolyzing diisopropoxy-bis(ethylacetoacetato)-titanium (I) by the addition of water, and then removing the isopropyl alcohol formed by the reaction by distillation. In this reaction the condensation stage 2, that is, where two equivalents of compound I react with one equivalent of water, should not be exceeded because longer chain condensates again tend to form precipitates or solidify at room temperature. If compound I is reacted with less water than that which corresponds to condensation stage 2, a mixture of condensed product and unchanged starting chelate I is formed which also behaves more favorably with respect to tendency towards crystallization than pure compound I. Therefore, the reaction of 2 mols of a titanium acetoacetate chelate with 1 mol of water is preferred, but the reaction with 0.5 to 1.0 mol water is also possible.

In practice, the titanium ester chelates according to the present invention can be prepared in a one-pot process by first reacting isopropyl titanate with acetoacetic acid ethyl ester and immediately afterward with water, and finally distilling off the isopropyl alcohol formed by the reaction. It is also possible to perform the reaction with water at a later time.

The subject matter of the present invention, therefore, are alcohol-free acetoacetic ester chelates of titanium, a process for their preparation, as well as their use as catalysts.

The dimer IA prepared by reaction of 2 mols of compound I with 1 mol of water remains liquid even at −25° C. over a period of several weeks. Even inoculation with crystals of compound I does not lead to spontaneous crystallization.

The situation is similar, although not quite so pronounced, in the case of triisopropoxy-ethylacetoacetatotitanium (II), that is, the reaction product of 1 mol of isopropyl titanate and 1 mol of acetoacetic acid ethyl ester. After distilling off the isopropanol formed by the reaction, crystals separate out of the initially liquid product upon standing at room temperature, and after cooling to +5° C. the entire product crystallizes throughout; upon subsequent standing at room temperature the crystalline product liquifies only to a very minor degree, even after 8 hours.

When 2 mols of compound II are admixed with 1 mol of water, which can take place only in dilution with isopropanol because of the lesser hydrolysis stability of the product, a liquid is obtained after distilling off the isopropanol from which no crystals separate out even after prolonged standing at room temperature. Thus, the condensed product (IIA) has also a lesser tendency toward crystallization and is therefore easier to handle. Upon cooling to +5° C. the liquid solidifies like glass with only very few crystalline areas, and after about 1 hour of subsequent standing at room temperature it is once again completely liquid.

In general, diisopropoxy-bis-(alkylacetoacetato)-titanium or triisopropoxy-alkylacetoacetato-titanium can be used as starting materials in which the alkyl radicals are identical or different radicals with 2 to 4 carbon atoms; the ethyl radical is preferred.

During the condensation one alkoxy group per titanium atom is split off as alcohol, so that a Ti-O-Ti bridge is formed and products of condensation stage 2 are formed. Especially advantageous is the preparation in the one-pot process by reaction of a tetraalkyl titanate with 1 or 2 mols of acetoacetic acid ester per titanium atom and subsequent addition of water, and removal of the alcohol by distillation. During the condensation the temperature of about 100° C. should not be exceeded.

Condensed products of the described type are capable as chelated titanates to cross link polymers with corresponding functional groups. Especially alcohol-free compounds such as compound IA can be used in silicone chemistry as components of hardening systems for silicones with terminal hydroxyl groups which are useful as sealing compounds.

The condensation stage of 2 means that two Ti-atoms are connected by an oxygen bridge —O— in every molecule. The formula is

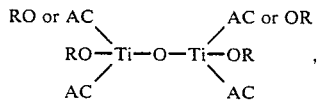

wherein AC means an alkylacetoacetato residue (=aceto acetato acid ester ligand) and OR alkoxy, R being 1 to 4 C-atoms.

EXAMPLE 1

(known substance—for reference purpose)

Diisopropoxy-bis(ethylacetoacetato)-titanium (I)

3,408 q (12 mol) of tetraisopropyl titanate were placed into a 10-liter flask equipped with a stirrer, thermometer, dropping funnel and condenser, and, while stirring, the contents were admixed over a period of 30 min with 3,120 g (24 mols) of acetoacetic acid ethyl ester, taking care that the temperature of the reaction mixture did not exceed 75° C. After stirring the mixture for another hour at about 70° C., the condenser was replaced by a distillation bridge and isopropanol Was distilled off (25 mm Hg/max. 90° C. sump temperature); 1,392 g isopropanol =98.2% of theory were obtained. 5,114 g of product I=100.5% of theory remained in the flask.

| | |
|---|---|
| Appearance: | orange-red liquid which crystallized after several hours or days. |
| Melting point: | about 28° C. |
| Density (35° C.): | about 1.09 g/ml |
| Viscosity (35° C.): | about 2 mPa.s |
| Refractive index (35° C.): | about 1.513 |

EXAMPLE 2

Condensation Product IA 1,136 g (4 mols) of tetraisopropyl titanate were introduced into a 4-liter flask equipped with a stirrer, a thermometer, a dropping funnel and a condenser, and the contents were admixed, while stirring, over a period of 10 min with 1.040 g (8 mols) of acetoacetic acid ethyl ester, whereby the temperature rose to 75° C. After rapid addition of 36 g (2 mols) of water the mixture was refluxed for 1 hour (sump temperature 88° C.), and then the condenser was exchanged for a distillation bridge and the alcohol in the mixture was distilled off in vacuo (toward the end 25 mm Hg/90° C. sump temperature); 659 g of alcohol =92% of theory were obtained. 1,554 g of product IA =104% of theory were obtained (caused by the partial conversion of the ethyl ester into the isopropyl ester).

Appearance: Red liquid
Density (20° C.): about 1.15 g/ml
Viscosity (20° C.): about 55 mpa.s
Refractive Index (20° C.): about 1.526

Said theoretical values correspond to the formula $C_{30}H_{50}O_{15}Ti_2$, wherein no ester conversion is considered. Two aceto acetato ester ligands and one isopropoxy group per Ti-atom are contained and two Ti-atoms are connected by an —O—bridge.

| | |
|---|---|
| Elemental Analysis: | C 48.2%, H 7.3%, Ti 12.3% |
| Averages Theoretical Values: | C 48,3%, H 6.7%, Ti 12.8% |
| Behavior Upon Cooling: | After standing for several days at −25° C. the product remains liquid. |

EXAMPLE 3

(known substance—for reference purpose)

Triisopropoxy-ethylacetoacetato-titanium (II)

426 g (1.5 mols) of tetraisopropyl titanate were placed into a 1-liter flask equipped with a stirrer, a thermometer a dropping funnel and a condenser, and, while stirring, the contents were admixed over a period of 20 minutes with 195 g (1.5 mols) of acetoacetic acid ethyl ester, during which the temperature rose to 57° C. After stirring the mixture for another hour at 75 to 80° C. the condenser was exchanged for a distillation bridge, and the isopropanol formed by the reaction was distilled off in vacuo (toward the end 12 mm Hg/72° C. sump temperature). 93 g of isopropanol =about 100% of theory were obtained. 525 g =98.9% of theory of product II remained in the flask in the form of an orange liquid out of which crystals separated after a few hours of standing.

| | |
|---|---|
| Density (20° C.): | about 1.059 g per/ml |
| Viscosity (20° C.): | about 130 mPA.s |
| Refractive index (20° C.): | about 1.510 |
| Behavior upon cooling: | After several hours of standing at +5° C. the liquid crystallized throughout. After another 8 hours of standing at room temperature only 5 to 10% of the crystals had melted. |

EXAMPLE 4

Condensation product IIA 284 g (1 mol) of tetraisopropyl titanate were introduced into a 1-liter flask equipped with a stirrer, a thermometer, a dropping funnel and a condenser, and, while stirring, the contents were admixed over a period of 10 min with 130 g (1 mol) of acetoacetic acid ethyl ester, during which the temperature rose to 59° C. After briefly heating the, reaction mixture to 75° C. it was cooled to 50° C. and a mixture of 9 g (0.5 mol) of water and 240 g of isopropanol was added thereto over a period of 30 min. After stirring the mixture for 1 hour at 70° C. the alcohol was distilled off in vacuo (toward the end 15 mm Hg/57° C. sump temperature), yielding 36g=100% of theory of isopropanol. 303 g of product IIA = 100% of theory in the form of an orange liquid remained in the flask.

| | |
|---|---|
| Density (20° C.): | about 1.129 g per/ml |
| Viscosity (20° C.): | about 220 mPa.s |
| Refractive index (20° C.): | about 1.533 |
| Behavior upon cooling: | After standing for several hours at +5° C. the liquid first solidified became liquid again. |

| Formula: | $C_{24}$ | $H_{46}O_{11}$ | $Ti_2$ |
|---|---|---|---|
| | C 47.5% | H 7.6% | Ti 15.8% |
| found: | C 47.% | H 7.8% | Ti 15.6% |

EXAMPLE 5

Cross-linking of silicon polymers

In the use of silicon polymers with terminal hydroxyl groups in sealing compositions, two criteria—among many others—must be observed which are directly connected with the cross-linking of the individual molecules into high polymeric elastomers: stability and virtually complete unalterability of the product in the storage vessel under exclusion of air, and sufficiently rapid hardening upon contact with the humidity of the air.

In order to test whether the product IA according to this invention (see Example 2) meets these criteria, the following test methods were chosen:

Skin forming test: time period from spreading of the silicone mass in a thin layer on a substrate until formation of skin (no tackiness when touched).

Flow test: Powder bottles were about ⅓ filled with the silicone masses, tightly closed and turned upside down. The time period is measured which elapses from turning the bottles right side up until the contents flow back to their original position.

Test materials: Commercial silicone polymer with terminal hydroxyl groups (1500 mPa.s);

Additive 1: 20% by weight solution of product IA in toluene;

Additive 2: 20% by weight solution of a 1:2-mixture of methyl-tris-(ethylmethylketoximo)-silane and product IA in toluene;

Additive 3: 50% by weight solution of the above mixture in toluene.

Test compositions: The silicone polymer is rapidly admixed by stirring with the amounts of additives 1 to 3 shown in the table below, and is immediately locked in an air-tight storage vessel.

| Results: Additive: | Amount % by wt. | skin formation time: | flow time after | | | |
|---|---|---|---|---|---|---|
| | | | 1 hour | 1 day | 2 days | 3 wks. |
| 1 | 3 | 6 min | 7 min | 8 min | — | 7 min |
| 2 | 3 | 1 hour 10 min | 3 min | 4.5 min | — | 8 min |
| 3 | 2 | 14 min | — | 20 min | 60 min | — |
| Comparison: | | Silicone without additive | 10 s | 15 s | — | 10 s |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A cold-resistant, alcohol-free chelate of titanium-(IV) of the formula

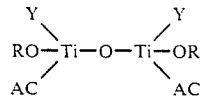

wherein Y is RO or AC,
R is alkyl of 1 to 4 carbon atoms, and
AC is an alkylacetoacetato radical.

2. The method of preparing a titanium chelate of claim 1, which comprises reacting a titanium ester selected from the group consisting of diisopropoxy-bis(ethylacetoacetato)-titanium and triisopropoxy-ethylacetoacetato-titanium with 0.5 to 1 mol of water per 2 mols of titanium ester starting material, and removing the alcohol formed by the reaction from the reaction mixture of distillation.

3. The method of preparing a titanium chelate of claim 1, which comprises sequentially reacting tetraisopropyl titanate with acetoacetic acid ethyl ester and with 0.5 and 1 mole of water per 2 mols of titanium ester starting material, and subsequently removing the alcohol in the reaction mixture by distillation.

* * * * *

UNITED STATES PATENT AND TRADEMARK OFFICE
CERTIFICATE OF CORRECTION

PATENT NO. : 4,924,016

DATED : May 8, 1990

INVENTOR(S) : Dieter Barfurth et al

It is certified that error appears in the above-identified patent and that said Letters Patent is hereby corrected as shown below:

Column 3, line 34, "3,408 q" should read --3,408 g--.

Column 3, line 42, "Was" should read --was--.

Column 4, last line, "36 g" should read --361 g--.

Signed and Sealed this

Third Day of March, 1992

Attest:

HARRY F. MANBECK, JR.

Attesting Officer     Commissioner of Patents and Trademarks